US00RE38169E

(19) United States
(12) Reissued Patent
Swenson

(10) Patent Number: US RE38,169 E
(45) Date of Reissued Patent: Jul. 1, 2003

(54) HYPERSTABILIZING ANTISENSE NUCLEIC ACID BINDING AGENTS

(75) Inventor: David H. Swenson, Midland, MI (US)

(73) Assignee: Board of Supervisors of Louisana State University and Agricultural and Mechanical College, Baton Rouge, LA (US)

(21) Appl. No.: 09/616,640

(22) Filed: Jul. 26, 2000

Related U.S. Patent Documents

Reissue of:
(64) Patent No.: 5,786,138
Issued: Jul. 28, 1998
Appl. No.: 08/289,130
Filed: Aug. 11, 1994

U.S. Applications:

(63) Continuation of application No. 08/010,408, filed on Jan. 29, 1993, now abandoned.

(51) Int. Cl.[7] ..... C12Q 1/68; C07D 293/10; C07H 21/02

(52) U.S. Cl. ..... 435/6; 435/5; 435/91.1; 435/91.2; 536/23.1; 536/24.3; 536/24.33; 536/24.5; 514/44; 548/121; 421/121

(58) Field of Search ..... 435/5, 6, 91.1, 435/91.2; 536/23.1, 24.3, 24.33, 24.5; 514/44; 548/121; 421/121

(56) References Cited

U.S. PATENT DOCUMENTS

| | | | | |
|---|---|---|---|---|
| 4,169,888 A | 10/1979 | Hanka et al. | ..... | 424/121 |
| 4,921,788 A | 5/1990 | Deutsch | ..... | 435/6 |
| 5,340,716 A | 8/1994 | Ullman et al. | ..... | 435/6 |

OTHER PUBLICATIONS

Boger, D. et al., "CC–1065 Partial Structures," *J. Org. Chem.*, vol. 57, pp. 1277–1284 (1992).
Boger et al., "Synthesis and Evaluation of Aborted and Extended CC–1065 Functional Analogues," J. Am. Chem. Soc., vol. 112, pp. 4623–4632 (1990).
Cohen, "Oligonucleotides as Therapeutic Agents," Pharmac. Ther., vol. 52, pp. 211–225 (1991).
Gura "Antisense has Growing Pains," pp. 575–577 (1995).
Hélène, "Artificial Control of Gene Expression by Oligodeoxynucleotides Covalently Linked to Intercalating Agents," Br. J. Cancer, vol. 60, pp. 157–160 (1989).
James, "Antiviral Chemistry and Chemotherapy," 2, pp. 191–214 (1991).
Kim et al., Dissertation Abstracts Int. 55 (3B), p. 829 (1993).
Krueger et al., "The Binding of CC–1065 to Poly– and Oligonucleotides," Biopolymers, vol. 24, pp. 1549–1572 (1985).
Lee et al., "Interaction of Psoralen–Derivatized Oligodeoxyrlbonucleoside Methylphosphonates with Single–Stranded DNA," Biochemistry, vol. 27, No. 9, pp. 3197–3203 (1988).
Lee et al., "Molecular Recognition between Oligopeptides and Nucleic Acids," J. Am. Chem. Soc., vol. 110, pp. 3641–3649 (1988).
Lewin, B., Genes IV, Chapter 5, "The Topology of Nucleic Acids," Oxford University Press, pp. 82–84 (1990).
Miller et al., "Anticancer Drug Design," 2, pp. 117–128 (1987).
Reynolds et al., "The Chemistry, Mechanism of Action and Biological Properties of CC–1065, A Potent Antitumor Antibiotic," J. Antibiotics, vol. 39, No. 3, pp. 319–334 (1986).
Roberts et al., "Stability and Properties of Double and Triple Helices: Dramatic Effects of RNA or DNA Backbone Composition," Science, vol. 258, pp. 1463–1466 (1992).
Swenson et al., "Mechanism of Interaction of CC–1065 (NSC 298223) with DNA," Cancer Research, vol. 42, pp. 2821–2828 (1982).
Uhlmann et al., "Antisense Oligonucleotides: A New Therapeutic Principle," Chemical Reviews, vol. 90, No. 4, pp. 543–584 (1990).
Wilson et al., Biochemistry, 32, pp. 4098–4104 (1993).
Witung et al., NAR vol. 22, pp. 5371–5377 (1994).
E. Lukhtanov et al., "Oligodeoxyribonucleotides with conjugated dihydropyrroloindole oligopeptides: Preparation and hybridization properties," *Bioconjugate Chem.*, vol. 6, pp. 418–426 (1995).
Boger, D., "CC–1065 and the duocarmycins . . . ," *Proc. Natl. Acad. Sci. USA*, vol. 92, pp. 3642–3649 (1995).
Boger, D. et al., "CC–1065 Partial Structures . . . ," *J. Org. Chem.*, vol. 57, pp. 1277–1284 (1992).
Boger, D. et al., "Studies on the Total Synthesis of CC1065 . . . ," *J. Org. Chem.*, vol. 52, pp. 1521–1530 (1987).
Fisher, J. et al., "The chemistry of DNA modification by antitumor antibiotics," *Prog. Drug Res.*, vol. 32, pp. 411–498 (1988).
Hurley, L. et al., "Approaches toward the design of sequence–specific drugs for DNA," in R. Allen (Ed.), *Ann. Rept. Med. Chem.*, vol. 22, pp. 259–268 (1987).
Swenson et al, "Evaluation of DNA binding characteristics of some CC–1065 analogs", Chemico–biological interactions 67(3–4) 199–213 ABSTRACT ONLY, 1988.*
Lee et al., "Structural and dynamic aspects of binding of a prototype lexitropsin to the decadeoxyribonucleotide (dCGCAATTGCG)2 deduced from high resolution 1H NMR studies" Biochemistry 27:445–455, 1988.*
Hurley et al, "Sequence specificity of DNA alkylation by the unnatural enantiomer of CC–1065 and its synthetic analogues", J. Am. Chem. Soc. 112:4633–4649, 1990.*

* cited by examiner

*Primary Examiner*—Jeffrey Fredman
(74) *Attorney, Agent, or Firm*—John H. Runnels

(57) ABSTRACT

Attaching certain ligands to antisense probes will hyperstabilize sense-antisense duplexes. Such a hyperstabilized duplex is resistant to melting of the strands from one another, to unwinding of the strands, and to the action of nucleases. Applications include antiretroviral action, antireverse-transcriptase action, antiviral action, antiparasitical action, antibacterial action, antifungal action, anticancer action, anti-oncogene action, and other applications where it is desired to inhibit gene expression at the genomic or messenger RNA level. The preferred ligands are certain minor-groove-binding agents, exemplified by CC-1065 and synthetic CC-1065 analogs.

39 Claims, No Drawings

HYPERSTABILIZING ANTISENSE NUCLEIC ACID BINDING AGENTS

Matter enclosed in heavy brackets [ ] appears in the original patent but forms no part of this reissue specification; matter printed in italics indicates the additions made by reissue.

This application is a continuation of application Ser. No. 08/010,408 filed Jan. 29, 1993, now abandoned.

This invention pertains to sense-antisense nucleic acid complexes, particularly to sense-antisense nucleic acid complexes which are hyperstabilized with a selective binding agent.

Nucleic acids, which encode the genetic information of all cells and viruses, commonly occur in two forms, known as DNA and RNA. A chain of several bases of RNA or DNA is called an oligonucleotide or a polynucleotide, depending on its size. Two oligonucleotides or polynucleotides whose base sequences are complementary to one another can bind to one another into a double helix through a process called base-pairing.

So-called "antisense" oligonucleotides or probes have been investigated as a possible means for regulating gene expression. An antisense oligonucleotide is an oligonucleotide (usually a synthetic oligonucleotide introduced from an external source) whose sequence is complementary to that of a target sequence of DNA or RNA (usually RNA) of a cell or virus. Because the antisense probe is complementary to the target sequence, the two can bind into a double helix. This induced double helix inhibits the activity of the target sequence, at least temporarily. The inhibition can result from failure of the RNA-DNA heteroduplex to be recognized as a template for translation, or as a result of the activation of RNase H by the RNA-DNA duplex. RNase H hydrolyses RNA in an RNA/DNA duplex. RNase H occurs in some viruses including HIV, bacteria, and ubiquitously in plant and animal cells. Thus RNA bound in such an RNA/DNA heteroduplex can be inactivated either because it is not recognized as a single-stranded messenger RNA, or because it is hydrolyzed after the heteroduplex forms.

Antisense technology is expected to have important therapeutic applications directed toward a variety of diseases, possibly including cancer, viral and retroviral diseases, autoimmune diseases, and parasitic infections.

Some structurally modified antisense probes have also been tested for potential therapeutic activity. These modifications generally render them resistant to nucleases, enzymes which degrade nucleic acids. These modifications are most commonly made to the phosphodiester linkage connecting adjacent nucleotides, but some sugar analogs and "artificial" stereoisomers of sugar-base linkages have also been devised.

Unfortunately, the resulting increase in nuclease resistance has been offset by a reduction in the stability of the sense-antisense duplex. A more stable sense-antisense duplex would permit smaller doses of antisense oligonucleotides to be used with greater effect. Previous strategies to enhance the stability of sense-antisense duplexes have included the attachment of intercalating acridines or reactive agents such as alkylating agents or psoralens (which is photoactive), but these approaches have met with only limited success.

Prior antisense technologies relying on the exogenous application of antisense oligonucleotides have encountered problems with the stability of the antisense probe, with the uptake of the antisense probes by cells, and with the stability of the sense-antisense duplexes formed. The first of these limitations, stability of the probe, is believed to be due to the susceptibility of single-stranded nucleotides (with conventional phosphodiester or PO linkages) to digestion by nucleases present in serum and in cell culture medium. The second limitation, uptake of the probes by cells, is believed to be due to poor uptake of the polyanionic (i.e., electronically charged) oligonucleotide through the cell membrane, although some studies have suggested the existence of an "oligonucleotide pump" which may transport charged oligonucleotides. Modified internucleotide linkages, such as those using methyl phosphonate (MP) or phosphorothioate (PS) linkages, have partially overcome the first two limitations. These modifications can result in improved resistance to nucleases, and somewhat enhanced cell penetration. See Uhlmann et al., "Antisense Oligonucleotides: A New Therapeutic Principle," Chemical Reviews, vol. 90, no. 4, pp. 543–584 (1990); and Cohen, "Oligonucleotides as Therapeutic Agents," Pharmac. Ther., vol. 52,pp. 211–225 (1991), the entire disclosures of both of which are incorporated by reference.

But treating the first two limitations has increased the difficulties caused by the third limitation, the problem of poor stability of sense-antisense hybrids (as measured by $T_m$, the strand separation temperature). With methylphosphonate antisense structures, an additional problem was also found: the antisense-sense duplexes did not stimulate RNase H.

Uhlmann et al., "Antisense Oligonucleotides: A New Therapeutic Principle," Chemical Reviews, vol. 90, no. 4, pp. 543–584 (1990) review generally the field of antisense technology, including the use of modified backbones in the oligonucleotides; the tethering of intercalating agents and psoralen; effects on RNase H activation; and limitations and strengths of the prior antisense technology.

Hélène, "Artificial Control of Gene Expression by Oligodeoxynucleotides Covalently Linked to Intercalating Agents," Br. J. Cancer, vol. 60, pp. 157–160 (1989); and Lee et al., "Interaction of Psoralen-Derivatized Oligodeoxyribonucleoside Methylphosphonates with Single-Stranded DNA," Biochemistry, vol. 27, no. 9, pp. 3197–3203 (1988) discuss the use of crosslinking agents (such as psoralens and alkylators) and acridines linked to antisense oligonucleotides, with limited increases observed in the resulting stabilization of the duplexes.

Cohen, "Oligonucleotides as Therapeutic Agents," Pharmac. Ther., vol. 52, pp. 211–225 (1991) discusses uses of oligonucleotides as therapeutic agents, including uses in triple-strand binding. Cohen noted that precious approaches to antisense technology have been more successful in preventing translation than in preventing elongation.

Reynolds et al., "The Chemistry, Mechanism of Action and Biological Properties of CC-1065, A Potent Antitumor Antibiotic," J. Antibiotics, vol. 39, No. 3, pp. 319–334 (1986) reviews the properties of CC-1065 and routes for its synthesis.

There is a need for a means to enhance the stability of sense-antisense complexes. Enhancement of sense-antisense duplexes would have at least two benefits: first, the duplexes would not separate as readily, increasing the effective length of time that the target is made unavailable for processes such as translation or (reverse) transcription; second, the concentration of the antisense probe required for a given level of activity should decrease.

If the stability of sense-antisense helices were improved, the increased stability would allow lower concentrations of antisense probes to show higher biological efficacy.

It has been discovered that binding certain ligands to antisense probes will hyperstabilize sense-antisense duplexes. Such a hyperstabilized duplex is resistant to melting of the strands from one another, and is believed to be resistant to unwinding of the strands and to the action of nucleases.

Applications of this discovery include, but are not limited to, the following: antiretroviral action, anti-reverse-transcriptase action, antiviral action, antiparasitical action, antibacterial action, antifungal action, anticancer (anti-oncogene) action, and other applications where it is desired to inhibit gene expression at the genomic or messenger RNA level.

These ligands are certain minor-groove-binding agents, exemplified by CC-1065, and synthetic CC-1065 analogs. The structure of CC-1065 is shown below:

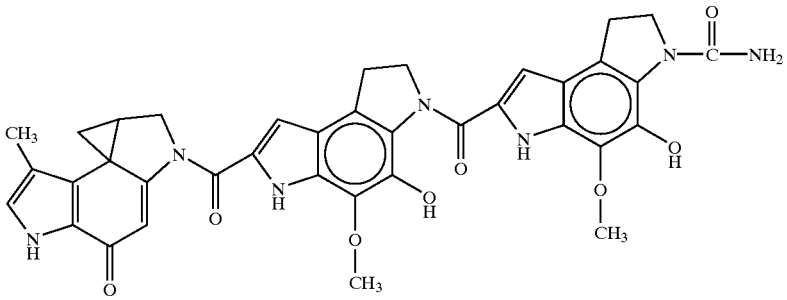

The production and purification of CC-1065 are described in U.S. Pat. No. 4,169,888, the entire disclosure of which is incorporated by reference. Note that CC-1065 comprises three tricyclic groups known as the A, B, and C subunits, from left to right, respectively, in the above structure. The A subunit is sometimes called the "CPI" component, for cyclopropylspirocyclohexadienone.

Minor-groove binders are known to stabilize DNA—DNA duplexes, but it was not previously known that similar effects could be obtained with RNA/DNA duplexes made with phosphodiester-, phosphorothioate-, or methyl phosphonate-based probes; or with DNA/DNA duplexes having a phosphorothioate, or methyl phosphonate backbone. In fact, it was previously thought that CC-1065 and its analogs would bind only B-form duplexes, and not A-form duplexes. RNA/DNA heteroduplexes have generally been thought to be A-form, and not B-form. Thus it is an unexpected result that CC-1065 can even bind an RNA-DNA (non-homopolymeric) heteroduplex. Krueger et al., "The Binding of CC-1065 to Poly- and Oligonucleotides," Biopolymers, vol. 24, pp. 1549–1572 (1985); cf. Roberts et al., "Stability and Properties of Double and Triple Helices: Dramatic Effects of RNA or DNA Backbone Composition," Science, vol. 258, pp. 1463–66 (1992) (not admitted to be prior art).

Initial studies have used CC-1065, a fermentation product of Streptomyces zelensis. CC-1065 was chosen because it is known to elevate the strand separation temperature, or $T_m$, of DNA or AT-rich DNA duplexes. ($T_m$ is the midpoint of the temperature range at which the two strands of the duplex separate from one another to become single-stranded, and is a measure of the strength of the binding of the two strands to one another.) CC-1065 does not bind single-stranded nucleic acids. CC-1065 binds double-stranded nucleic acids with a degree of sequence selectivity. Because its binding is sequence-selective, the sense strand may be targeted by judicious selection of the sequence from the target genome. The biological activity of CC-1065 appears to be due to its ability to hyperstabilize DNA against the melting and unwinding processes that are required for replication.

The present invention permits the complete inactivation of target genes, target messenger RNA (mRNA), or target retroviral genomic RNA. An antisense probe is chemically CC-1065; netropsin; possibly distamycin (a non-covalent binding agent) and other lexitropsins (see Lee et al., "Molecular Recognition between Oligopeptides and Nucleic Acids," J. Am. Chem. Soc., vol. 110, pp. 3641–3649 (1988), the entire disclosure of which is incorporated by reference); other peptide-based minor-groove binding agents; aryl and heteroaryl oligomers (see Braithwaite et al., Biochemistry, vol. 19, pp. 1101 et seq. (1980), the entire disclosure of which is incorporated by reference); quaternary amine-containing reagents (See Boger et al., "CC-1065 Partial Structures," J. Org. Chem., vol. 57, pp. 1277–1284 (1992) (not admitted to be prior art), the entire disclosure of which is incorporated by reference); and other minor groove binding agents which can engage in van der Waals, covalent, hydrogen, or ionic bonding with the duplex. Preferred are those minor groove binding agents which exhibit at least a degree of sequence selectivity. Certain major-groove binding agents are also expected to work in the present invention; for example a nucleic acid oligomer which will form a triple helix by entering the major groove of a double helix may be an appropriate ligand, although the tether would likely have to be longer. The size of the antisense sequence will depend on factors such as reaction rate, stability, and uniqueness of the target sequence; they will typically be 10 to 30 bases long.

A preferred ligand, a modification of CC-1065 which has been named "tristabilin," is shown below:

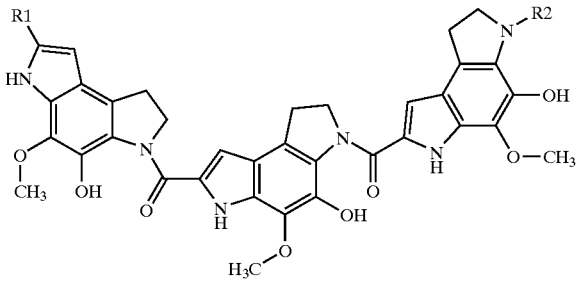

R1 and R2 denote groups which may be useful in the tethering. R1 may be, for example, —H, —$NH_2$, or —COOH. R2 may be, for example, —H or a blocking group such as t-BOC or acyl.

The binding specificity of CC-1065 and its analogs in the minor groove has a consensus target sequence of 5'-RNTTA-3' or 5'-AAAAA-3', where R denotes A or G; and N denotes A, C, G, T, or U. This consensus sequence is a loosely defined consensus sequence, as there are efficient binding sites which do not match this consensus pattern. Examples of efficient binding sites which do not fit this consensus pattern include 5'-GACTA-3' and 5'-TATTA-3'. Thus a strategy using this class of compound should accommodate the sequence preference of the drug. CC-1065 and U-71,184 react covalently with the N-3 of the 3'-adenine in the consensus sequence through the cyclopropyl function. Alkylation by the cyclopropyl group in the A-ring system in CC-1065 is thought to be destabilizing, even for the duplex-ligand complex. This fact, and the desire to eliminate promiscuous attack of the ligand on nontarget sequences, makes CC-1065-like agents composed of two through four, preferably three, identical (or similar) ring systems (that do not engage in covalent interactions) preferred minor-groove binding agents.

In the claims below, a binding agent which is said to "preferentially bind" in the minor groove of a particular double helix is one having a degree of selectivity for a sequence or subsequence within that particular minor groove; i.e., one which will bind at least one sequence of subsequence in that minor groove substantially more strongly or rapidly than it would, on average, bind a randomly selected minor groove sequence of the same length. In other words, there need not be perfect selectivity, but there must be a sequence or subsequence in the minor groove which the binding agent will bind more strongly than would be expected, on average, through chance. (This definition will also apply by analogy to major groove binding agents.)

CC-1065 was observed to bind to part of a 20-mer sequence taken from the env gene of the equine infectious anemia (EIA) retrovirus (sense sequence). Such binding was observed both with antisense probes made with normal phosphodiester backbones, as well as those made with modified backbones comprising phosphorothioate, or methyl phosphonate. A chemically synthesized RNA sense sequence was prepared, and appeared to be a target for binding CC-1065 when the RNA was duplexed with any of these three antisense probes.

Experiments were also performed with polyadenylic acid (poly(rA)) and oligo(dT) (a synthesized 20-mer). CC-1065 bound to these duplexes, although not as well as it bound to oligo(dA)-oligo(dT) duplexes. Strand separation temperatures ($T_m$) were determined for the adducted DNA sense sequences duplexed with the three antisense types, for adducted poly(rA)-oligo(dT), and for oligo(dA)-oligo(dT). In all cases, the $T_m$ was elevated. (The low purity of the commercial RNA sample used in these studies precluded the measurement of $T_m$ values for duplexes from these species.)

By contract, experiments with Distamycin A gave a significant elevation of $T_m$ only with oligo(dA)-oligo(dT). With U-71,184, $T_m$ elevations were observed for all the duplexes evaluated, except poly(rA)-oligo(dT). The structure of U-71,184 is shown below:

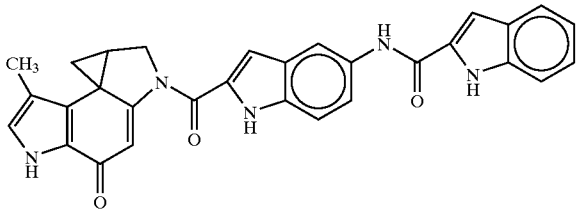

These findings suggest that the non-CPI components of CC-1065 are important in the stabilization of RNA-DNA duplexes. It should also be possible to target mRNA (and possibly DNA) with various derivatives of CC-1065. Suitable derivatives would include those based on two to four, preferably three, sets of hydroxy, methoxypyrroloindole-type or pyrrolomethoxyhydroxyindole-type tricyclic rings, as exemplified by the B ring of CC-1065. Further, a similar complex should target DNA, but not mRNA, if a U-71,184 derivative is used as the stabilizing ligand. Such U-71,184 derivatives might include those in which one or more of the functional groups which are "missing" in comparison with CC-1065 are added to the U-71,184 structure, such as the hydroxy, methoxy, and the methylenes associated with the pyrrole. The derivatives of CC-1065 or of U-71,184 as described above may be synthesized through standard means known in the art; see also the discussion below concerning the synthesis of a preferred derivative of CC-1065.

Distamycin analogs (lexitropsins) are expected to have limited applicability.

Experiments have also shown that CC-1065, in the presence of an antisense probe, can completely arrest translation in vitro.

It is believed that the CPI (A-ring system) of CC-1065 may not be a strong contributor to the non-covalent interactions of the compound with minor groove DNA sites, and that it may in fact destabilize non-covalent binding. Thus its replacement with a ring system such as the B and C systems of CC-1065 may give a better agent for duplex stabilization, particularly where the ligand is tethered to the antisense sequence in such a fashion that it can freely fit into and bind with the minor groove sites. Replacement of the CPI with a non-covalent functional group will also reduce the promiscuity of attack on random, nontarget sequence. Systems having two to four, preferably three, tricyclic rings are expected to be particularly promising, as discussed above. See, e.g., the following paper, the entire disclosure of which is incorporated by reference: Boger et al., "Synthesis and Evaluation of Aborted and Extended CC-1065 Functional Analogues," J. Am. Chem. Soc., vol. 112, pp. 4623–4632 (1990).

In a preferred embodiment, an antisense sequence (containing within it a sequence compatible with the preferred binding sequence(s) of the ligand) is tethered to a ligand comprising a non-CPI-containing CC-1065 analog. This combination provides a "gene-lock" that physically blocks an RNA (or DNA) sequence from engaging in its normal functions, such as transcription, reverse transcription, or translation.

The "tethering" of a minor-groove binding agent to the antisense oligonucleotide is performed in a manner that permits the binding agent to enter the minor groove upon duplex formation, and to bind there. Conversely, the structure of the tethered minor-groove-binder may help direct duplex formation of the desired mRNA or DNA targets. The tethered agents optionally have an integral alkylating moiety that act to fix the agent in the groove. Whether an alkylating moiety should be included in a given situation depends on such factors as the degree of stabilization which is achieved without alkylation, and the potential promiscuity of the ligand toward nontarget sequences. Because the alkylating subunit of CC-1065 is potentially destabilizing, better overall performance may be achieved by deleting the alkylating functional group. Deleting this group has another advantage as well: without the alkylating group, any non-specific binding that may occur will eventually dissociate without damage to the non-target sequence, reducing the impact of any promiscuous binding that may occur.

Minor-groove-binding agents such as netropsin, distamycin, CC-1065, and related analogs can enhance helix stability, as measured by $T_m$. For example, distamycin has been reported to increase the $T_m$ of poly(dA)-poly(dT), but distamycin does not covalently bind DNA. CC-1065, which covalently binds to AT-rich sites in DNA, has been reported to raise the $T_m$ to near 100° C. for both calf thymus DNA and for poly(dA)-poly(dT), representing an increase in $T_m$ of over 30° C. under the conditions of the experiment.

CC-1065 binds a region spanning five base pairs in the minor groove of a double helix. As mentioned above, CC-1065 has a degree of sequence selectivity for AT-rich regions. But this partial selectivity in itself is inadequate to target specific sequences. Other minor-groove binders also appear to have a general preference for AT-rich sites. The binding of such agents to DNA appears to have a long-range stabilizing effect for ten to twenty bases on either side of the actual binding site. See Swenson et al., "Mechanism of Interaction of CC-1065 with DNA," Cancer Research, vol. 42, pp. 2821–2882 (1982), the entire disclosure of which is incorporated by reference. It is believed that the hyperstabilized DNA interferes with the melting and unwinding processes which are required for normal DNA function.

There are at least two ways to view the tethering of a minor-groove binding agent to an antisense probe. (The two views in fact are essentially equivalent to one another.) One is that the binding agent has superb targeting to a specific sequence that contains a favorable binding subsequence, where it can specifically exert its genotoxic or anti-message effects. The other is to view the tethering as a method for hyperstabilizing an antisense-sense complex, using the ligand as the stabilizing tool. The sense sequence can, for example, be part of an mRNA, an HIV molecule, or a region of genomic DNA. In addition to targeting pathogens, the sense sequence may target a region of genomic DNA which is over-expressed, or whose expression is otherwise desired to be suppressed. DNA may also be targeted with a tethered ligand (such as an oligonucleotide) that forms a triple-stranded helix that may be hyperstabilized.

Many drugs that bind in the minor groove of double-stranded DNA and hyperstabilize the helix will also do so with helices in which one strand comprises an MP or a PS backbone; with helices formed between RNA and DNA; and with helices in which the RNA sense strand is complexed with an MP or PS antisense probe.

A variety of agents can bind in the minor groove of double-stranded DNA to AT-rich sites, thereby increasing the $T_m$ of DNA duplexes. RNA or poly(rA)-poly(rU) do not bind CC-1065 well. Poly(rA)-poly(dT) is a good substrate, however, and an RNA-DNA hybrid of appropriate composition was shown to be a target for CC-1065 binding. DNA and AT-rich synthetic poly- and oligodeoxyribonucleotide duplexes were found to be excellent substrates for binding. Further, the stability of DNA and the synthetic DNA duplexes was significantly enhanced, as indicated by $T_m$ studies.

No tethered antisense-minor groove binding species (with or without covalent attachment groups) have, to the inventor's knowledge, been previously made or tested. Furthermore, no known prior work has discussed the binding of minor-groove-binding drugs to oligonucleotides with a modified phosphate backbone. Crosslinking agents (such as psoralens and alkylators) and acridines have been linked to antisense oligonucleotides, with limited increases in the stabilization of the duplexes. See Lee et al., "Interaction of Psoralen-Derivatized Oligodeoxyribonucleoside Methylphosphonates with Single-Stranded DNA," Biochemistry, vol. 27, no. 9, pp. 3197–3203 (1988); and Hélène, "Artificial Control of Gene Expression by Oligodeoxynucleotides Covalently Linked to Intercalating Agents," Br. J. Cancer, vol. 60, pp. 157–160 (1989).

CC-1065 was chosen for initial trails in free-solution binding studies. This agent was chosen because it forms a covalent bond with A sites in DNA, thereby modelling the effect of a tethered drug. A 20-mer region of the equine infectious anemia virus (EIAV) envelope gene (env) was chosen as the target sequence. This sequence, 5'-TTACTTCAGTTATGAGACCA-3' (SEQ ID NO. 1), has a 5'-AGTTA-3' site in the center, a pentamer known to be a good target for CC-1065. The antisense sequence, 3'-AATGAAGTCAATACTCTGGT-5' (SEQ ID NO. 2), has an adjacent binding site 3'-AATGA-5', which will also be bound by CC-1065. Covalent bond formation occurs at the N-3 position of the 3'-A in the respective pentamers.

Oligodeoxyribonucleotides were obtained by chemical synthesis through standard techniques on an automated synthesizer located in the Department of Veterinary Microbiology and Parasitology at Louisiana State University. Antisense MP and PS oligonucleotides were obtained from commercial sources, as was synthetic sense RNA. Poly(rA) was obtained from Sigma Chemical Co. CC-1065 was obtained from the Upjohn Company. Oligonucleotides (0.075 $\mu$mol-P each) were mixed in 0.36 ml 0.01 M Na cacodylate buffer, pH 7.2, with CC-1065 in dimethyl formamide (0.04 ml), or with dimethylformamide only. (Note that "μmol-P" denotes μmoles of phosphate; i.e., μmoles of nucleotide bases, rather than of oligonucleotides per se.) Incubations of complementary strands, with or without drug, were carried out at 37° C. for 4 hr. In the initial experiments, unbound drug was separated from nucleotide duplexes by ethanol precipitation. Equivalent results were obtained by trapping the oligonucleotides and CC-1065 on NACS-52 columns, and washing first with low-salt buffer and then with buffer containing 1M NaCl. Unbound CC-1065 was completely retained on the column. Both methods gave identical results, and mixing the methods did not reduce binding of CC-1065. Samples prepared in this manner could be directly used for determination of binding of the drug to the nucleic acid (as measured by the $A_{365}/A_{260}$ ratio), with the extinction of CC-1065 absorbance at 365 nm taken as 48,000, and the extinction of the nucleic acid absorption at 260 nm based on its composition. Similar approaches were used with the drug U-71,184, with an assumed extinction of 32,000 at 365 nm.

When methyl phosphonate and synthetic RNA were used, the purities of the crude oligonucleotides were taken to be about 30%, based on the data sheet prepared by the supplier. (The remainder comprised primarily truncated sequences.) Appropriate excess amounts of these agents were included in the reactions to ensure helix formation. The corresponding sense or antisense oligonucleotides were maintained at 0.075 μmol-P in the reaction. Because CC-1065 binds only to double-stranded nucleic acids, and was found not to bind to single-stranded materials under the conditions used, total binding of CC-1065 to the duplexes was estimated by measuring the amount of CC-1065 eluted with the nucleic acid fraction, and by comparing it to known recovery rates for nucleic acids eluted on the same type of column. Unpurified materials were used in these preliminary studies because of the relatively high cost of purified oligoribonucleotides. The majority of the contributions to $A_{260}$ for these samples should be due to material that was not duplexed.

Samples for determining $T_m$ were also obtained by the above procedures. Distamycin does not covalently bind to nucleic acids, and cannot readily be run through a chromatographic column without dissociating from the nucleic acids. Thus the effects of this agent on $T_m$ were carried out with Distamycin in solution with the duplexes tested.

$T_m$'s were determined on a Gilford 2400 Spectrophotometer set at 260 nm, with a 4-chamber Peltier-based temperature controller. Temperature was ramped linearly at 0.5° C./min. Absorbance data were acquired with a 12-bit A/D converter, and data were processed with Lotus 123W and SigmaPlot software. $T_m$ values were determined from the plots as the midpoint of the thermal transitions.

Table 1 summarizes binding data obtained from incubations of CC-1065 with nucleotides at greater than stoichiometric levels; the levels used in these experiments were 1 drug molecule/10 nucleotide residues, which is equivalent to 4 drug molecules/20-mer duplex. The results shown in Table 1 demonstrate that CC-1065 will bind to duplexes in which one strand has a modified phosphate backbone. There seemed to be no difference in drug binding between antisense oligonucleotides with a PO and those with a PS backbone. Again, the 5'-AGTTA-3' sequence on the sense strand was presumably the primary target, and the 3'-AAGTA-5' on the antisense probe was presumably the secondary target.

TABLE 1

Saturation Binding of CC-1065 to Duplexes

| Sense[1] Type | Antisense[2] Type | Approx. No. CC-1065 Bound/20 Base Pairs[3] |
|---|---|---|
| DNA | DNA-PO[4] | 2 |
| DNA | DNA-PS | 2 |
| DNA | DNA-MP | 1 |
| Oligo(dA) | Oligo(dT) (PO)[5] | 2.5 |
| Poly(rA) | Oligo(dT) (PO)[5] | 1 |
| RNA | DNA-PO | 1 |
| RNA | DNA-PS | 1 |
| RNA | DNA-MP | Not Done |
| Salmon Sperm DNA | | 2 |

Notes to Table 1:

Equimolar amounts of sense and antisense strands (totalling 0.15 μmol nucleotides) were reacted with 0.015 μmol CC-1065 (in 0.04 ml DMF) in 0.36 ml Na cacodylate - 1 mM EDTA buffer (0.01 M, pH 7.2) at 37° C. for 4 hr. The nucleic acids were isolated by trapping on a NACS column. The NACS column was eluted with the Na cacodylate buffer (containing 0.1M NaCl), and the nucleotides were eluted with 0.01M Na cacodylate buffer containing 1M NaCl. Unbound CC-1065 remained bound to the column. When RNA sense or MP antisense sequences were used, higher concentrations of those species were employed to accomodate their estimated 30% purity. The amount bound was estimated from the amount of CC-1065 eluting with the nucleotide fraction; duplex recovery was based on recovery of the other duplexes. With MP antisense oligonucleotides, titration with a range of MP gave an estimate of 1 molecule bound per duplex. Precipitation with NaCl and EtOH gave similar results, but recoveries were lower. Single-strand components did not bind CC-1065.

Additional notes to Table 1:

[1]The sense strand had the sequence 5'-TTACTTCAGTTATGAGACCA-3' (SEQ ID NO. 1), unless otherwise specified. The sense and antisense sequences are from the env gene of the equine infectious anemia retrovirus.

[2]The antisense strand had the sequence 3'-AATGAAGTCAATACTCTGGT-5' (SEQ ID NO. 2), unless otherwise specified.

[3]The initial CC-1065/nucleotide ratio was 0.1, equivalent to 4 drug molecules per duplex.

[4]The nomenclature used here is "PO" for normal phosphodiester bond ("O" signifies oxygen atom on phosphorous), "PS" for 100% phosphorothioate in the internucleotide bond, and MP for methyl phosphonate internucleotide bond.

[5]"Oligo(dA)" and "Olig(dT)" refer to 20-mers synthesized with normal phosphodiester chemistries.

However with an MP backbone, the binding appeared to be limited to one site per duplex. It is believed that the potential 3'-AAGTA-5' site on the MP strand was not targeted, because this site is a less avid binding site for CC-1065. With the RNA sense sequence, the single binding site is likely to be the central targeted site.

The data in Table 2 also show that an RNA sense sequence is capable of binding CC-1065 in the presence of PO or PS antisense oligonucleotides.

Table 2 presents more details on the binding studies for the DNA sense targets, and for the homocopolymers.

TABLE 2

Binding of CC-1065 to Duplexes

| Initial D/N[2] | Final D/N (CC-1065/nucleotide) Bound to Duplex[1] | | | | |
|---|---|---|---|---|---|
| | PO-PO[3] | PO-PS | PO-MP | Oligo(dA)-Oligo(dT) | Poly(rA)-Oligo(dT) |
| 0.01 | 0.009 ± 0.0004 | 0.010 ± 0 | not done | 0.008 ± 0.001 | 0.003 ± 0.002 |
| 0.025 | 0.021 ± 0.001 | 0.024 ± 0.0005 | 0.016 ± 0.0008 | 0.018 ± 0.0006 | 0.008 ± 0.004 |
| 0.04 | 0.030 ± 0.0004 | 0.032 ± 0.001 | 0.019[4] | 0.028 ± 0.006 | 0.011 ± 0.004 |
| 0.065 | 0.049 ± 0.001 | 0.047 ± 0.0005 | not done | 0.058 ± 0.002 | 0.022 ± 0.004 |
| 0.10 | 0.053 ± 0.002 | 0.049 ± 0 | 0.031 ± 0.001 | 0.063 ± 0.002 | 0.028 ± 0.001 |

Notes to Table 2:
Equimolar amounts of sense and antisense strands (totalling 0.15 μmol nucleotides) were reacted with 0.015 μmol CC-1065 (in 0.04 ml DMF) in 0.36 ml Na cacodylate - 1 mM EDTA buffer (0.01 M, pH 7.2) at 37° C. for 4 hrs. The nucleic acids were isolated by trapping on a NACS column. The NACS column was eluted with the Na cacodylate buffer (containing 0.1M NaCl), and the nucleotides were eluted with 0.01M Na cacodylate buffer containing 1M NaCl. Unbound CC-1065 remained bound to the column. When RNA sense or MP antisense sequences were used, higher concentrations of those species were employed to accomodate their estimated 30% purity. The amount bound was estimated from the amount of CC-1065 eluting with the nucleotide fraction; duplex recovery was based on recovery of the other duplexes. Precipitation with NaCl and EtOH gave similar results, but recoveries were lower. Single-strand components did not bind CC-1065.
Additional notes to Table 2:
[1]Triplicate values except as noted.
[2]D/N = Drug molecules/nucleotide.
[3]The nomenclature used is:
"PO-PO" denotes phosphodiester sense, phosphodiester antisense, both DNA;
"PO-PS" denotes phosphodiester DNA sense, phosphorothioate antisense;
"PO-MP" denotes phosphodiester DNA sense, methylphosphonate antisense.
[4]Single determination instead of triplicate value.

The effects of CC-1065 with an antisense probe on the translation of a fragment of the env gene of EIAV are shown in Table 3. The concentration of antisense oligomers alone was high enough to partially inhibit translation, but the further addition of CC-1065 to the antisense oligomer and mRNA essentially prevented translation (Tube 5). The counts obtained were at background for the assay (complete assay without mRNA present). Further, autoradiography of the samples showed a suppressed production of the two protein products from the translation with antisense oligomers alone; whereas the combination of antisense oligomers and CC-1065 completely suppressed product under the conditions of the assay (data not shown).

The in vitro translation studies were performed as follows. A fragment of DNA from the env gene of EIAV was transcribed with an SP-6 polymerase kit, and the resulting mRNA (approximately 600 bases long) was capped and isolated. The transcribed fragment included the target sequence 5'-TCAACCCCTATTACCCAACA-3' (SEQ ID NO. 3) (the CC-1065 binding site is underlined). The corresponding antisense sequence (using normal phosphodiester chemistry) was 5'-TGTTGGGTAATAGGGGTTGA-3' (SEQ ID NO. 4). Translation was performed with a wheat-germ extract (Promega) in the presence of $^{35}$S-methionine. The mRNA's were divided into approximately 2 μg aliquots, and treated according to the protocols listed for Table 3 below. Treated mRNA was separated from small molecules (such as DMSO and CC-1065) with a Sephadex 50-based NICK column. Translation was carried out in 25 μl of buffer containing the wheat germ translation system; the isolated mRNA; amino acids, including the labelled methionine; and RNAsin, an inhibitor of RNase. The proteins produced were divided into two aliquots. One aliquot was fractionated by SDS-PAGE, followed by autoradiography; and the other was analyzed by scintillation spectrometry. The concentrations of antisense oligomers and CC-1065 in the free-solution chemistries were relatively high compared to the sense target, to optimize duplex formation and drug binding. The following pairs of reactions did not give statistically different results at the P<0.05 level by Student's t-test: 1,2; 1,3; 1,4; 2,3; 2,4. The following pairs were different at the P<0.05 level by Student's t-test (unpaired analysis): 1,5; 2,5; 3,4; 3,5; 4,5.

TABLE 3

| Tube No. | mRNA (μl)[1] | DMSO | CC-1065 DMSO (μl)[2] | Antisense (μl)[3] | Purpose of Tube | DPM S-35 ± standard error |
|---|---|---|---|---|---|---|
| 1 | 1.95 | 0 | 0 | 0 | determine maximum | 124,990 ± 40,810 |
| 2 | 1.95 | 5 | 0 | 0 | effect of DMSO | 144.260 ± 46.325 |
| 3 | 1.95 | 0 | 5 | 0 | effect of CC-1065 | 133.040 ± 13.227 |
| 4 | 1.95 | 0 | 0 | 1.8 | effect of antisense | 35.225 ± 3.667 |
| 5 | 1.95 | 0 | 5 | 1.8 | effect of antisense and CC-1065 | 8.720 ± 3.787 |

Notes to Table 3:

TABLE 3-continued

| Tube No. | mRNA (μl)[1] | DMSO | CC-1065 DMSO (μl)[2] | Antisense (μl)[3] | Purpose of Tube | DPM S-35 ± standard error |
|---|---|---|---|---|---|---|

[1]1.95 μg of mRNA was subjected to treatment prior to isolation for translation studies.
[2]DMSO was the vehicle for the CC-1065, dimethyl formamide inhibited translation. The concentration of CC-1065 in the reaction was set at 3 times the concentration of antisense.
[3]Antisense concentrations in these free-solution chemistries were about three times the concentration of nRNA sense in the free-solution bindings. This concentration represents about a 90-fold excess on a per-target basis.

Table 4 shows that sense-antisense complexes with bound CC-1065 showed elevated $T_m$'s. The difference in $T_m$'s between control (D/N=0) and CC-1065-bound duplexes was statistically significant by Student's t-test (≦0.05 level). The ability of CC-1065 to stabilize an RNA-DNA duplex was shown by the ability of that drug to increase the $T_m$ of poly(rA)-poly(dT) in much the same way that it did the $T_m$ of oligo(dA)-oligo(dT).

TABLE 4

Duplex Strand Separation Temperatures With CC-1065

| Sense[1] Type | Antisense[2] Type | $T_m$ (° C.) at Various Initial Drug/Nucleotide (D/N) Ratios: D/N = 0 | D/N = 0.025 | D/N = 0.1 |
|---|---|---|---|---|
| DNA | DNA-PO[3] | 68.0 ± 0 | 81.7 ± 0.6[4] | 85.3 ± 2.3[4,5] |
| DNA | DNA-PS | 64.2 ± 1.5 | 81.3 ± 2.3[4] | 84.7 ± 1.5[4,5] |
| DNA | DNA-MP | 53.5 ± 4.5[6] | 73.0 ± 2.0[4] | 74.0 ± 1.0[4] |
| Oligo dA | Oligo dT (PO) | 57.0 ± 0 | 50 and 85[7] | 85.5 ± 0.7[4,5] |
| Poly rA | Oligo dT (PO)[8] | 53.0 ± 1.4[9] | 51 and 76[7] | 81.3 ± 0.6[4,5] |
| Reference $T_m$ taken in 0.1M NaCl (low salt) | | | | |
| DNA | DNA-PO | 55.5 ± 0.7 | | |
| DNA | DNA-PS | 53.5 ± 0.7 | | |
| Oligo dA | Oligo dT | 52.5 ± 0.7 | | |
| Effect of NaCl Concentration on $T_m$ of Salmon Sperm DNA | | | | |
| SS-DNA[10], No NaCl, buffer only | | 62 | | |
| SS-DNA, 0.1M NaCl, buffer | | 82 | | |

Notes to Table 4:
Equimolar amounts of sense and antisense strands (totalling 0.15 μmol nucleotides) were reacted with CC-1065 (in 0.04 ml DMF) in 0.4 ml Na cacodylate - 1 mM EDTA buffer (0.01 M, pH 7.2) at 37° C. for 4 hr. The nucleic acids were isolated by trapping on a NACS column. The NACS column was eluted with the Na cacodylate buffer (containing 0.1M NaCl) and the nucleotides were eluted with the 0.01M Na [cacadylate] *cacodylate* buffer containing 1M NaCl. Unbound CC-1065 remained bound to the column. After measuring the drug bound ($A_{365}$) to the nucleic acid ($A_{254}$), samples were stored at −20° C. until analyzed for $T_m$. See Table 2. $T_m$'s were measured in a Gilford 2400 UV/Vis spectrophotometer equipped with a Peltier-based Thermoset cuvette temperature controller, modified to allow temperature programming. Sample temperature was increased linearly at 0.5°/min.
Additional notes to Table 4:
[1]The sense strand had the sequence 5'-TTACTTCAGTTATGAGACCA-3' (SEQ ID NO. 1), unless otherwise specified. The sense sequence is from the env gene of the equine infectious anemia retrovirus.
[2]The antisense strand had the sequence 3'-AATGAAGTCAATACTCTGGT-5' (SEQ ID NO. 2), unless otherwise specified.
[3]The nomenclature used is "PO" for normal phosphodiester bond ("O" signifies oxygen atom on phosphorous); "PS" for 100% phosphorothioate in the internucleotide bond, and "MP" for methyl phosphonate internucleotide bond.
[4]P ≦ 0.05 by Student's t-test, compared to no drug.
[5]Melting not completed at termination of temperature ramp. These values represent minimum $T_m$ estimates.

TABLE 4-continued

Duplex Strand Separation Temperatures With CC-1065

| Sense[1] Type | Antisense[2] Type | $T_m$ (° C.) at Various Initial Drug/Nucleotide (D/N) Ratios: D/N = 0 | D/N = 0.025 | D/N = 0.1 |
|---|---|---|---|---|

[6]$T_m$ plot did not show sigmoid shape and was nearly linear, in contrast to drug-treated MP-containing duplexes.
[7]Biphasic curve, with regions lacking CC-1065 melting lower, and those with CC-1065 melting higher.
[8]"Oligo dA" and "Oligo dT" refer to 20-mers synthesized with normal phosphodiester chemistries.
[9]N = 2 samples.
[10]"SS-DNA" denotes commercial salmon sperm DNA.

Table 5 shows the ability of U-71,184 to bind duplexes formed with DNA sense sequences, and PO, PS and MP antisense sequences. Binding appeared to be about half that for CC-1065 with PO and PS antisense sequences, while binding for MP antisense sequences was similar for both agents (about 1 drug molecule/duplex). As with CC-1065, U-71,184 bound well to both homocopolymers.

TABLE 5

Binding of U-71.184 to Duplexes at Initial D/N = 0.10

| Duplex Type[1] | $T_m$ (° C.) at Initial Drug/Nucleotide = 0.1 Bound D/N[2] |
|---|---|
| PO-PO | 0.026 ± 0.004 |
| PO-PS | 0.026 ± 0.001 |
| PO-MP | 0.029 ± 0.001 |
| Oligo(dA)-Oligo(dT) | 0.049 ± 0.001 |
| Poly(rA)-Oligo(dT) | 0.023 ± 0.001 |

Notes to Table 5:
[1]As before, PO is phosphodiester. PS is phosphorothioate. MP is methyl phosphonate. The first term is the DNA sense and the second is the DNA antisense.
[2]D/N is Drug/Nucleotide ratio.

The effect of U-71,184 on the $T_m$'s of the duplexes (Table 6) was significantly different from that of CC-1065. First, the stabilizing effect of U-71,184 was observed to be less than that of CC-1065 for PO and PS antisense sequences, but it appeared to be as effective as CC-1065 with MP antisense sequences and with oligo(dA)-oligo(dT). The failure of U-71,184 to stabilize duplexes of poly(rA)-oligo(dT), compared to the strong stabilization by CC-1065, was unexpected in light of the effects which these two agents had on the other duplexes. The data in Table 6 suggest that CC-1065 or an analog may be more effective as a stabilizing agent than a U-71,184-like compound.

TABLE 6

Duplex Strand Separation Temperatures: U-71.184 vs. CC-1065

| Sense[1] Type | Antisense[2] Type | No Drug | U-71.184 | CC-1065 |
|---|---|---|---|---|
| DNA | DNA-PO[3] | 68.0 ± 0 | 75.5 ± 0.7 | 85.3 ± 2.3[4] |
| DNA | DNA-PS | 64.2 ± 1.5 | 73.0 ± 1.4 | 84.7 ± 1.5[4] |
| DNA | DNA-MP | 53.5 ± 4.5[5] | 73.0 ± 1.7 | 74.0 ± 1.04 |
| Oligo dA | Oligo dT | 57.0 ± 0 | 86.7 ± 0.6 | 85.5 ± 0.7[4] |
| Poly rA | Oligo dT (PO)[6] | 53.0 ± 1.4[7] | 54.3 ± 0.6 | 81.3 ± 0.6[4] |

Notes to Table 6:

Equimolar amounts of sense and antisense strands (totalling 0.15 μmol nucleotides) were reacted with CC-1065 (in 0.04 ml DMF) in 0.4 ml Na cacodylate - 1 mM EDTA buffer (0.01 M, pH 7.2) at 37° C. for 4 hr. The nucleic acids were isolated by trapping on a NACS column. The NACS column was eluted with the Na cacodylate buffer (containing 0.1M NaCl), and the nucleotides were eluted with 0.01M Na cacodylate buffer containing 1M NaCl. Unbound CC-1065 remained bound to the column. After measuring the drug bound ($A_{365}$) to the nucleic acid ($A_{254}$), samples were stored at −20° C. until analyzed for $T_m$. See Table 2. $T_m$'s were measured in a Gilford 2400 UV/Vis spectrophotometer equipped with a Peltier-based Thermoset cuvette temperature controller, modified to allow temperature programming. Sample temperature was increased linearly at 0.5°/min.

Additional notes to Table 4:

[1]The sense strand had the sequence 5'-TTACTTCAGTTATGAGACCA-3' (SEQ ID NO. 1), unless otherwise specified. The sense sequence is from the env gene of the equine infectious anemia retrovirus.

[2]The antisense strand had the sequence 3'-AATGAAGTCAATACTCTGGT-5' (SEQ ID NO. 2), unless otherwise specified.

[3]The nomenclature used is "PO" for normal phosphodiester bond ("O" signifies oxygen atom on phosphorous), "PS" for 100% phosphorothioate in the internucleotide bond, and "MP" for methyl phosphonate internucleotide bond.

[4]Melting not completed at termination of temperature ramp. These values represent minimum $T_m$ estimates.

[5]$T_m$ plot did not show sigmoid shape and was nearly linear, in contrast to drug-treated MP-containing duplexes.

[6]"Oligo dA" and "Oligo dT" refer to 20-mers synthesized with normal phosphodiester chemistries.

[7]N = 2 samples.

Distamycin A elevated the $T_m$ of essentially only oligo [(dA))-oligo(dT)] (*dA*)-*oligo*(*dT*), as is shown in Table 7. This finding was not expected. Distamycin does not covalently bind and its effects on $T_m$ were carried out as free-solution evaluations.

TABLE 7

$T_m$ Elevation by Distamycin in Solution at D/N = 0.1

| Duplex Type | Base $T_m$ | Ave ± S.D. | Increase in $T_m$ |
|---|---|---|---|
| PO-PO | 68.0 ± 0 | 68.7 ± 0.6 | 0.7 |
| PS-PS | 64.2 ± 1.5 | 65.7 ± 1.5 | 1.5 |
| PO-MP | 53.5 ± 4.5 | Not Done | Not Done |
| dA-dT | 57.0 ± 0 | 78.3 ± 0.6 | 21.3 |
| rA-dT | 53.0 ± 1.4 | 57.0 ± 0 | 4.0 |

Table 8 summarized the $T_m$ data for Distamycin, U-71, 184 and CC-1065. The summary data suggest that an antisense drug tethered to a U-71,184-like agent may be capable of targeting DNA sequences without interfering with RNA targets. To attack mRNA, the data suggest that a CC-1065-like ligand tethered to an antisense probe is preferred.

TABLE 8

Comparison of $T_m$ Elevation at Highest Level of Binding Obtained

| | $T_m$ Elevation (° C.) | | |
|---|---|---|---|
| Duplex Type | Distamycin | U-71.184 | CC-1065 |
| PO-PO | 0.7 | 7.5 | 17.3 |
| PS-PS | 1.5 | 8.6 | 20.5 |
| PO-MP | Not Done | 19.5 | 21.5 |
| dA-dT | 21.3 | 29.7 | 28.5 |
| rA-dT | 4.0 | 1.3 | 28.3 |

Improved results are expected with a ligand such as CC-1065, without a CPI unit, tethered to an antisense sequence. It is believed that the CPI component destabilizes the initial drug-duplex binding reaction. In addition, the CPI component may allow promiscuous attack by the ligand on nontarget sequences, causing unwanted side-effects.

The antisense structure chosen should reflect the use to which it will be put, as well as pertinent cost factors. For instance, if RNase H activation is desired, one would not choose an MP backbone, because duplexes with such a strand do not activate RNase H. A PO backbone will generally not be preferred, because such polymers tend to be inherently unstable in vivo. The tether need not necessarily be attached at one of the ends; it could also be attached internally. If one wishes to attach the ligand to a site on the phosphorous, then perhaps a modified phosphoramidate can be employed for the purpose. See, e.g., Uhlmann et al., "Antisense Oligonucleotides: A new Therapeutic Principle," Chemical Reviews, vol. 90, no. 4, pp. 543–584 (1990), the entire disclosure of which is incorporated by reference.

Modeling studies using a space-filling DNA model and precision molecular models (Molecular Design, Inc.) show that commercial heterobifunctional couplers can be used to link the oligonucleotide to the ligand. The oligonucleotide is preferably prepared with a terminal alkylamine (convertible to a thiol) or alkyl sulfhydryl function, and the ligand preferably has an available amine that can be acylated by the heterobifunctional coupler. One coupler to be used is the 14 carbon, 2 nitrogen linker "SIAXX" available from Molecular Probes, Inc. The polyamide nature of this linker assists both in water solubility and in the minor groove interactions. Water solubility can be an important factor in drug delivery.

Ligands with tricyclic ring systems are favored for further evaluation. A preferred ligand, which has been named "tristabilin," is shown below:

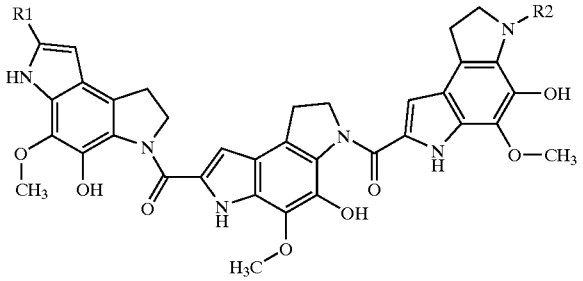

R1 and R2 denote groups which may be useful in the tethering. R1 may be, for example, —H, —$NH_2$, or —COOH. R2 may be, for example, —H, a reactive group such as 2-bromoacetyl or 2-mercaptoacetyl, or a blocking group such as t-BOC or acyl. This ligand will be synthesized, and tethered to antisense oligonucleotides via a tether with an appropriate terminal alkylamine linker. The optimum tether length will also be determined by elongating or shortening (up to 2 base residues in each case) the chain at the end of the molecule from which the linking terminus exists. This modification will have the effect of altering the linker arm length, without the confounding factor of differing linker structures. The optimum oligonucleotide-tether-ligand configuration will be evaluated by the $T_m$ of the duplex mixture and by gel electrophoresis. The optimum configuration thus determined will also be reconstructed with a phosphorothioate-based oligonucleotide backbone, which will be used in an assay to determine its ability to arrest translation.

It is expected that altering the length of the oligonucleotide so that the ligand falls short of its binding site will have a greater effect on stabilizing ability than will be the case where the ligand can reach past its optimum binding site. If the situation is such that the ligand cannot reach its preferred minor groove binding site, but hyperstabilization is nevertheless observed, then there may be a type of cross-linking between adjacent duplexes. Such cross-linking could be detected through gel electrophoresis. Rates of duplex formation and ligand binding can be readily determined by measuring the induced circular dichoroism (CD) spectrum for the helix, and at a separate wavelength, for the ligand.

The preferred ligand illustrated above will be synthesized and tethered to an antisense oligonucleotide. The ligand will be synthesized by following generally the route of Bolton et al., "Synthesis of the Phosphodiesterase Inhibitors PDE-I and PDE-II," J. Chem. Soc., Chem. Commun., pp. 1775–1776 (1985), which is incorporated by reference, to produce the following compound (R2=t-butylcarbonyl):

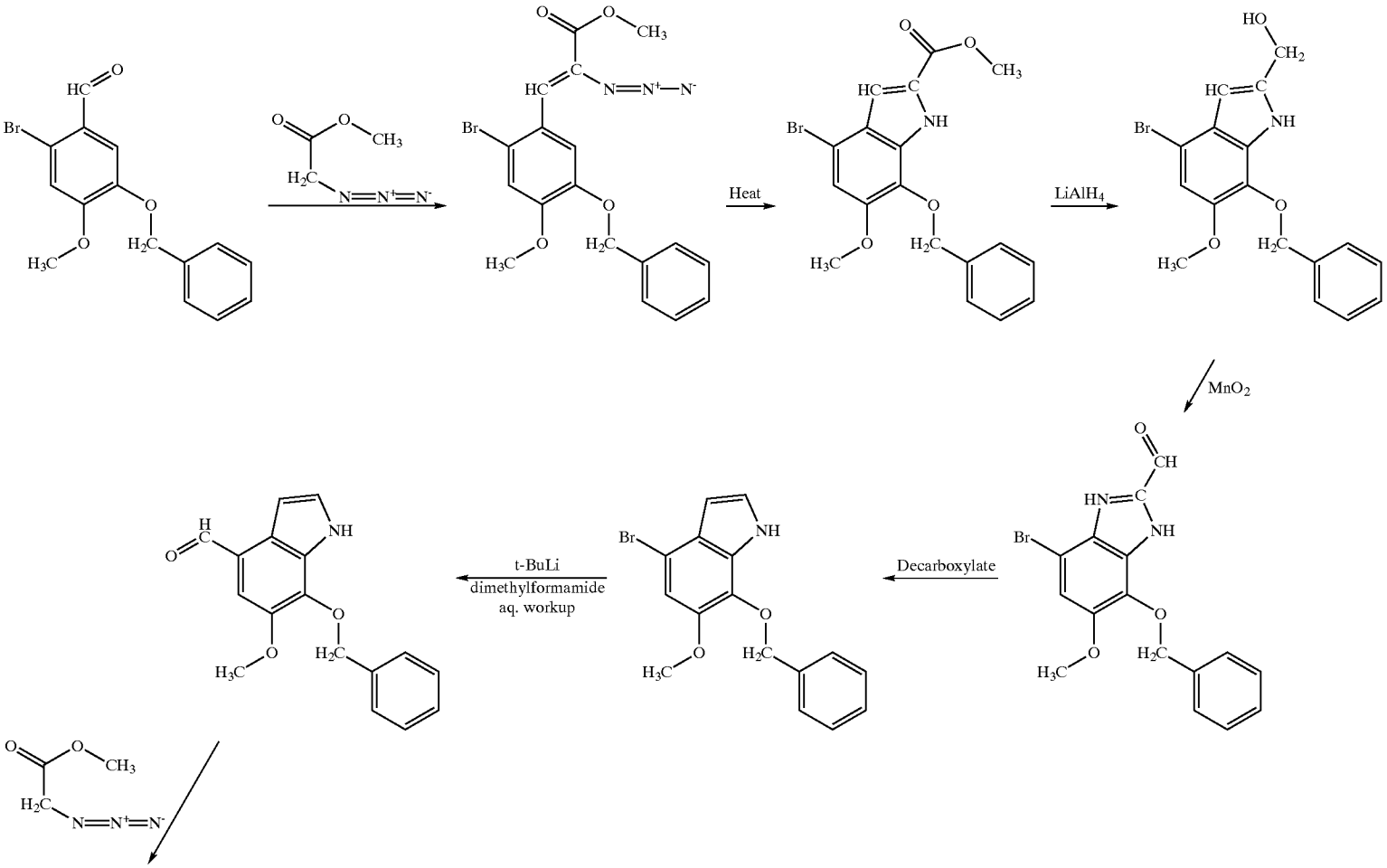
LiAlH4
MnO2
Heat
Decarboxylate
t-BuLi
dimethylformamide
aq. workup

-continued
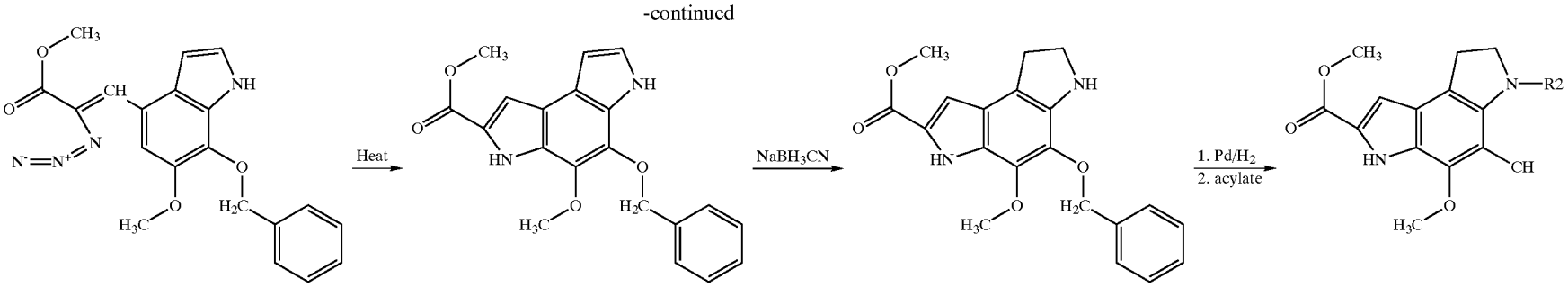

Possible alternative synthetic routes, whose disclosures are all also incorporated by reference, include those taught generally by Boger et al., "Diels-Alder Reactions of Heterocyclic Azadienes: Total Synthesis of PDE I, PDE II, and PDE I Dimer Methyl Ester," J. Am. Chem. Soc., vol. 109, pp. 2717–2727 (1987); Rawal et al., "Photocyclization Strategy for the Synthesis of Antitumor Agent CC-1065—Synthesis of the B and C Unit Fragments," J. Am. Chem. Soc., Vol. 108, pp. 2110–2112 (1986); Carter et al., "Studies on the Synthesis of the Antitumor Agent CC-1065—Synthesis of PDE I and PDE II, Inhibitors of cAMP Phosphodiesterase," J. Chem. Soc., Chem. Commun., pp. 1162–1164 (1986); and Reynolds et al., "The Chemistry, Mechanism of Action and Biological Properties of CC-1065, A Potent Antitumor Antibiotic," J. Antibiotics, vol. 39, no. 3, pp. 319–334 (1986), including each of the references cited therein.

The terminal compound from this synthesis will be selectively de-methylated with base, or the t-butyloxycarbonyl (t-BOC) group will be removed with acid, and the monomers will be coupled with standard amino acid coupling processes (see Boger et al., cited above) sequentially until the tris-tricyclic system has been synthesized. In the final step, only the t-BOC group will be removed (i.e., R2=H) to accommodate the tether. The t-BOC functional group will be immediately replaced with a mercaptoacetate group to provide a sulfhydryl group as a synthon for coupling the tricyclic ligand to the tether.

The linker or tether structure is dictated to some extent by what is readily available commercially that fits the structural needs. Those described in Brinkley, "A Brief Survey of Methods for Preparing Protein Conjugates with Dye Haptens, and Cross-Linking Reagents," Bioconjugate Chem., vol. 3, pp. 2 et seq. (1992) (not admitted to be prior art), the entire disclosure of which is incorporated by reference, will be tested. Using space-filling molecular models, it was found that attaching the linker arm to the 3'-end of the antisense oligonucleotide will allow penetration of ligand into the duplex about 2 bases further than would be the case if it were attached to the 5'-end. Thus linkages made to the 3'-end of the antisense oligonucleotide are thought to be preferred.

Antisense oligonucleotides can readily be synthesized with a propylamino analog attached through a 3'-phosphate, using a commercially available DNA synthesizer and standard techniques known in the art. An amino moiety on the oligonucleotide and a free thiol function on the ligand are chosen so that a heterobifunctional coupling agent may be used to control the directionality of the reaction. The SIAXX tether from Molecular Probes, Inc. which will be used initially is shown below, followed by a schematic depiction of the antisense-tether-ligand complex:

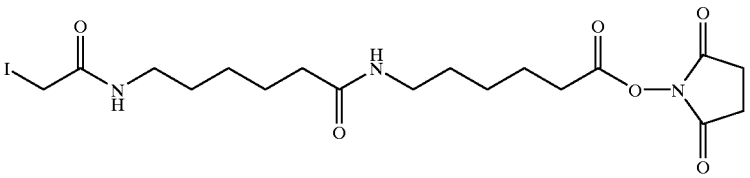

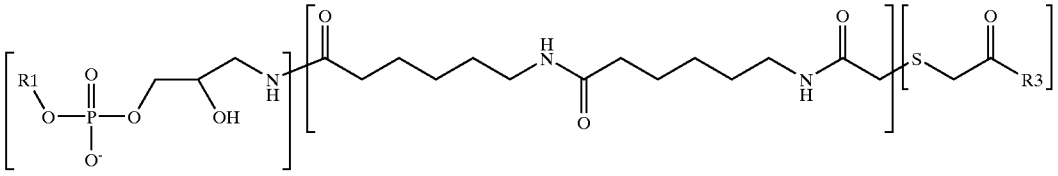

From Oligonucleotide Commercial Heterobifunctional Coupler Ligand

"SIAXX" is succinimidyl 6-(6-(((iodacetyl)amino) hexanoyl)amino) hexanoate. Its synthesis is described in Brinkley, "A Brief Survey of Methods for Preparing Protein Conjugates with Dye Haptens, and Cross-Linking Reagents," Bioconjugate Chem., vol. 3, pp. 2 et seq. (1992) (not admitted to be prior art), the entire disclosure of which is incorporated by reference.

Results of the 3'-linker studies will be compared to a study with a linker coupled to the 5'-end to determine the effect of ligand and linker orientation on binding and helix stabilization.

The full structure of the linker-ligand combination is shown below.

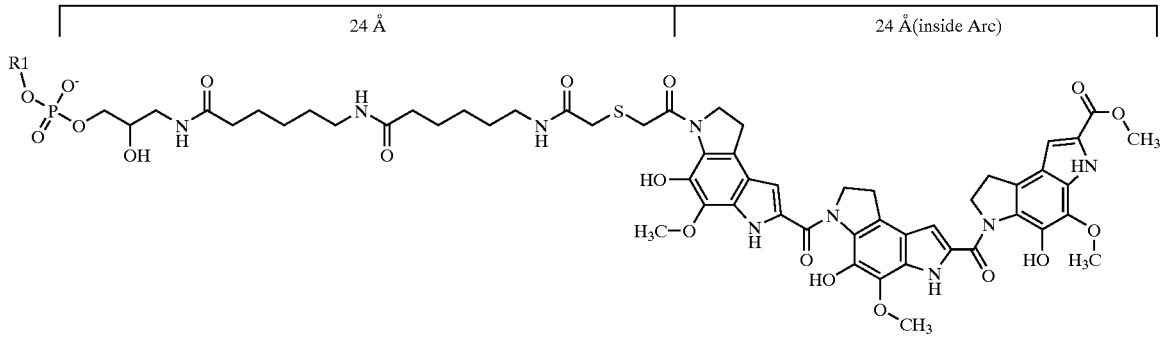

Although the linker is depicted above as a linear chain, model building with a space-filling DNA model shows that the linker will twist and curve to fit snugly in the minor groove. The linker and ligand have about the same molecular dimensions. The structure of the linker arm should facilitate minor-groove binding of the combination because of the van der Waals and hydrogen bonding contacts afforded by the polyamide structure. Binding in the major groove is not expected, as major-groove binding has not been reported for these classes of compounds.

To determine the optimum length of linker arm, rather than changing the length of the tether it is planned to progressively alter the location of the ligand binding site on the antisense chain. This approach will allow the experiments to be controlled for the potentially confounding factor of tether structure. For example, the antisense sequence 5'-TGACTGTTGGGTAATAGGGG-3' (SEQ ID NO. 5) (complementary ligand binding site underlined) may be shortened or lengthened at the 3'-end.

The effectiveness of the ligand as a stabilizing agent will be determined by comparing $T_m$ for the sense-antisense-ligand complex with $T_m$ for the sense-antisense duplex only; this approach compensates for the effects of differing chain lengths. Table 9 shows the expected effects of each substitution. The X shown at the 3'-end of the antisense oligonucleotide is the linker-ligand. The optimum target is underlined, and the expected location of the ligand is shown in bold, italic type.

TABLE 9

Proposed Antisense-Tether-Ligand Combinations

| Sense-Antisense Complex | Expected Location of Ligand | Expected Effect on $T_m$ |
|---|---|---|
| 5'-TCAACCCCTATTACCCAACA<br>3'-X-GGGGATAATGGGTTGT<br>(SEQ ID NOS. 3 & 6) | On target site. | Optimum increase in $T_m$ cf. sense-antisense only. |
| 5'-TCAACCCCTATTACCCAACA<br>3'-X-TGGGGATAATGGGTTGT<br>(SEQ ID NOS. 3 & 7) | Left of target site; may be unable to extend to site. | Significantly less than optimum $T_m$. |
| 5'-TCAACCCCTATTACCCAACA<br>3'-X-TTGGGGATAATGGGTTGT<br>(SEQ ID NOS. 3 & 8) | Significantly left of target site. May bind poorly. | Little or no increase in $T_m$. |
| 5'-TCAACCCCTATTACCCAACA<br>3'-X-GGGATAATGGGTTGT<br>(SEQ ID NOS. 3 & 9) | Linker may "bulge" slightly to accommodate binding. | Slightly less than optimum $T_m$. |
| 5'-TCAACCCCTATTACCCAACA<br>3'-X-GGATAATGGGTTGT<br>(SEQ ID NOS. 3 & 10) | Linker may "bulge" greatly to accommodate binding. | Significantly less than optimum $T_m$. |
| 5'-TCAACCCCTATTACCCAACA<br>3'-AGTTGGGGATAATGG-X<br>(SEQ ID NOS. 3 & 11) | On target site; 5'-linker. | Optimum increase in $T_m$; same as for 3'-linker. |

In addition to the expected "perfect fit" sense-antisense-ligand situation, Table 9 outlines a plan to make and test two "too-short" tether-ligand combinations, and two "too long" combinations. In addition, a single "perfect fit" 5'-tethered antisense-ligand combination will be evaluated to compare to the corresponding 3'-tethered "perfect fit" combination.

The stability of the duplexes will also be determined. $T_m$ will be measured for all duplexes. Non-denaturing polyacrylamide gel electrophoresis (with ethidium staining) will be carried out to ensure that agglomeration does not occur. Agglomeration might occur if suboptimal linkage lengths did not permit self-association, but did permit the ligand to bind to, and stabilize, other duplexes, thereby tying one or more duplexes together. Under such circumstances, one might observe doubling, tripling, etc. of the apparent size of the duplexes.

The rate of duplex formation, and the interaction of the ligand in the helix of optimal configurations will be followed by measuring the induced circular dichroism (CD) spectrum for the ligand. The stability of the ligand in the minor groove will be followed by CD, using Distamycin to displace the ligand, and determining the concentration of Distamycin required to displace 50% of the ligand.

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Equine infectious anemia virus (xi) SEQUENCE DESCRIPTION: SEQ ID NO: 1:

TTACTTCAGT TATGAGACCA 20

(2) INFORMATION FOR SEQ ID NO: 2:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(A) ORGANISM: Synthetic (xi) SEQUENCE DESCRIPTION: SEQ ID NO: 2:

TGGTCTCATA ACTGAAGTAA 20

(2) INFORMATION FOR SEQ ID NO: 3:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Equine Infectious Anemia Virus (xi) SEQUENCE DESCRIPTION: SEQ ID NO: 3:

TCAACCCCTA TTACCCAACA 20

(2) INFORMATION FOR SEQ ID NO: 4:

(i) SEQUENCE CHARACTERISTICS:
(A) LENGTH: 20 base pairs
(B) TYPE: nucleic acid

-continued (C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(A) ORGANISM: Synthetic (xi) SEQUENCE DESCRIPTION: SEQ ID NO: 4:

TGTTGGGTAA TAGGGGTTGA 20

(2) INFORMATION FOR SEQ ID NO: 5:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(A) ORGANISM: Synthetic (xi) SEQUENCE DESCRIPTION: SEQ ID NO: 5:

TGACTGTTGG GTAATAGGGG 20

(2) INFORMATION FOR SEQ ID NO: 6:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(A) ORGANISM: Synthetic (xi) SEQUENCE DESCRIPTION: SEQ ID NO: 6:

TGTTGGGTAA TAGGGG 16

(2) INFORMATION FOR SEQ ID NO: 7:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(A) ORGANISM: Synthetic (xi) SEQUENCE DESCRIPTION: SEQ ID NO: 7:

-continued

TGTTGGGTAA TAGGGGT 17

(2) INFORMATION FOR SEQ ID NO: 8:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(A) ORGANISM: Synthetic (xi) SEQUENCE DESCRIPTION: SEQ ID NO: 8:

TGTTGGGTAA TAGGGGTT 18

(2) INFORMATION FOR SEQ ID NO: 9:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(A) ORGANISM: Synthetic (xi) SEQUENCE DESCRIPTION: SEQ ID NO: 9:

TGTTGGGTAA TAGGG 15

(2) INFORMATION FOR SEQ ID NO: 10:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (vi) ORIGINAL SOURCE:
(A) ORGANISM: Synthetic (xi) SEQUENCE DESCRIPTION: SEQ ID NO: 10:

TGTTGGGTAA TAGG 14

(2) INFORMATION FOR SEQ ID NO: 11:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

-continued

```
(iii) HYPOTHETICAL: NO

(iv) ANTI-SENSE: YES

(vi) ORIGINAL SOURCE:
     (A) ORGANISM: Synthetic

(xi) SEQUENCE DESCRIPTION: SEQ ID NO: 11:

GGTAATAGGG GTTGA                                                    15
```

I claim:

1. A composition [for binding a selected ribonucleic acid sequence which is not a homopolymer,] comprising:

(a) an oligonucleotide which is not a homopolymer, and which is complementary to [the] *a* selected ribonucleic acid sequence *which is not a homopolymer*, and which can base-pair to the selected ribonucleic acid sequence to form a double helix having a minor groove and a major groove; and (b) a *non-alkylating* binding agent which preferentially binds in the minor groove of a double helix formed by the base-pairing of said oligonucleotide and the selected ribonucleic acid sequence, and which increases the strand separation temperature of the double helix; wherein said binding agent is selected from the group consisting of [CC-1065,] tristabilin, an agent comprising [a pyrrolomethoxy hydroxyindole] *from two to four pyrrolomethoxyhydroxyindole* tricyclic [ring, U71,184, an indole, an indole] *rings, an agent comprising from two to four indoles, an agent comprising from two to four indoles* substituted with at least one hydroxy group, an [indole] *agent comprising from two to four indoles* substituted with at least one methoxy group, [an indole] *and an agent comprising from two to four indoles* substituted with at least one pyrrole[, and a lexitropsin].

[2. A composition for binding a selected ribonucleic acid sequence which is not a homopolymer, comprising:

(a) an oligonucleotide which is not a homopolymer, and which is complementary to the selected ribonucleic acid sequence, and which can base-pair to the selected ribonucleic acid sequence to form a double helix having a minor groove and a major groove; and (b) a binding agent which preferentially binds in the minor groove of a double helix formed by the base-pairing of said oligonucleotide and the selected ribonucleic acid sequence, and which increases the strand separation temperature of the double helix, wherein said binding agent is chemically tethered to said oligonucleotide.]

[3. A composition as recited in claim 1, wherein said binding agent comprises CC-1065.]

4. A composition as recited in claim [3,] *1*, wherein said binding agent is chemically tethered to said oligonucleotide.

5. A composition as recited in claim 4, wherein said binding agent and said oligonucleotide are each covalently bound to succinimidyl 6-(6-(((iodoacetyl) amino) hexanoyl) amino) hexanoate.

6. A composition as recited in claim 1, wherein said binding agent comprises tristabilin.

7. A composition as recited in claim 6, wherein said binding agent is chemically tethered to said oligonucleotide.

[8. A composition as recited to claim 1, wherein said binding agent comprises a pyrrolomethoxyhydroxyindole tricyclic ring.]

[9. A composition as recited in claim 8, wherein said binding agent is chemically tethered to said oligonucleotide.]

10. A composition as recited in claim [8,] *1*, wherein said binding agent comprises three pyrrolomethoxyhydroxyindole tricyclic rings.

11. A composition as recited in claim 10, wherein said binding agent is chemically tethered to said oligonucleotide.

12. A composition as recited in claim [8,] *1*, wherein said binding agent comprises two pyrrolomethoxyhydroxyindole tricyclic rings.

13. A composition as recited in claim 12, wherein said binding agent is chemically tethered to said oligonucleotide.

14. A composition as recited in claim [8,] *1*, wherein said binding agent comprises four pyrrolomethoxyhydroxyindole tricyclic rings.

15. A composition as recited in claim 14, wherein said binding agent is chemically tethered to said oligonucleotide.

[16. A composition as recited in claim 1, wherein said binding agent comprises U-71,184.]

[17. A composition as recited in claim 16, wherein said binding agent is chemically tethered to said oligonucleotide.]

18. A composition as recited in claim 1, wherein said binding agent comprises [an indole, or an indole] *from two to four indoles, or from two to four indoles* substituted with at least one functional group selected from the group consisting of hydroxy, methoxy, and pyrrole.

19. A composition as recited in claim 18, wherein said binding agent is chemically tethered to said oligonucleotide.

[20. A composition as recited in claim 1, wherein said binding agent comprises a lexitropsin.]

21. A composition as recited in claim [20,] *1, wherein said binding agent comprises a lexitropsin, and* wherein said binding agent is chemically tethered to said oligonucleotide.

22. A composition [for binding a selected ribonucleic acid sequence which is not a homopolymer, comprising:] *as recited in claim 1,*

[(a) an oligonucleotide which is not a homopolymer, and which is complementary to the selected ribonucleic acid sequence, and which can base-pair to the selected ribonucleic acid sequence to form a double helix having a minor groove and a major groove,] wherein said oligonucleotide contains internucleotide bonds which comprise phosphorothioate or methyl phosphonate[; and]

[(b) a binding agent which preferentially binds in the minor groove of a double helix formed by the base-pairing of said oligonucleotide and the selected ribonucleic acid sequence, and which increases the strand separation temperature of the double helix].

23. A composition as recited in claim 22, wherein said binding agent is chemically tethered to said oligonucleotide.

24. An in vitro method for binding a selected ribonucleic acid sequence which is not a homopolymer, comprising the steps of:

(a) contacting the selected ribonucleic acid sequence in vitro with an oligonucleotide which is not a homopolymer, and which is complementary to the selected ribonucleic acid sequence, and which can base-pair to the selected ribonucleic acid sequence to form a double helix having a minor groove and a major groove, until such a double helix is formed; and (b) contacting the double helix in vitro with a *non-alkylating* binding agent which preferentially binds in the minor groove of the double helix, and which increases the strand separation temperature of the double helix, until said binding agent has bound in the minor groove*; wherein the binding agent is selected from the group consisting of tristabilin, an agent comprising from two to four pyrrolomethoxyhydroxyindole tricyclic rings, an agent comprising from two to four indoles, an agent comprising from two to four indoles substituted with at least one hydroxy group, an agent comprising from two to four indoles substituted with at least one methoxy group, and an agent comprising from two to four indoles substituted with at least one pyrrole*.

25. A method as recited in claim 24, wherein said binding agent is chemically tethered to said oligonucleotide.

[26. A method as recited in claim 24, wherein said binding agent comprises CC-1065.]

[27. A method as recited in claim 26, wherein said binding agent is chemically tethered to said oligonucleotide.]

[28. A method as recited in claim 27, wherein said binding agent and said oligonucleotide are each covalently bound to succinimidyl 6-(6-(((iodacetyl) amino) hexanoyl) amino) hexanoate.]

29. A method as recited in claim 24, wherein said binding agent comprises tristabilin.

30. A method as recited in claim 29, wherein said binding agent is chemically tethered to said oligonucleotide.

31. A method as recited in claim [30,] *24,* wherein said binding agent comprises [a] *from two to four* pyrrolomethoxyhydroxyindole tricyclic [ring] *rings*.

32. A method as recited in claim 31, wherein said binding agent is chemically tethered to said oligonucleotide.

33. A method as recited in claim 31, wherein said binding agent comprises three pyrrolomethoxyhydroxyindole tricyclic rings.

34. A method as recited in claim 33, wherein said binding agent is chemically tethered to said oligonucleotide.

35. A method as recited in claim 31, wherein said binding agent comprises two pyrrolomethoxyhydroxyindole tricyclic rings.

36. A method as recited in claim 35, wherein said binding agent is chemically tethered to said oligonucleotide.

37. A method as recited in claim 31, wherein said binding agent comprises four pyrrolomethoxyhydroxyindole tricyclic rings.

38. A method as recited in claim 37, wherein said binding agent is chemically tethered to said oligonucleotide.

[39. A method as recited in claim 24, wherein said binding agent comprises U-71,184.]

[40. A method as recited in claim 39, wherein said binding agent is chemically tethered to said oligonucleotide.]

41. A method as recited in claim 24, wherein said binding agent comprises [an indole, or an indole] *from two to four indoles, or from two to four indoles* substituted with at least one functional group selected from the group consisting of hydroxy, methoxy and pyrrole.

42. A method as recited in claim 41, wherein said binding agent is chemically tethered to said oligonucleotide.

[43. A method as recited in claim 24, wherein said binding agent comprises a lexitropsin.]

[44. A method as recited in claim 43, wherein said binding agent is chemically tethered to said oligonucleotide.]

45. A method as recited in claim 24, wherein said oligonucleotide contains internucleotide bonds which comprise phosphorothioate or methyl phosphonate.

46. A method as recited in claim 45, wherein said binding agent is chemically tethered to said oligonucleotide.

47. A composition of matter comprising tristabilin.

*48. A composition as recited in claim 4, wherein said binding agent is chemically tethered to said oligonucleotide at the 3' end of said oligonucleotide.*

*49. A composition as recited in claim 4, wherein said binding agent is chemically tethered to said oligonucleotide at the 5' end of said oligonucleotide.*

*50. A composition as recited in claim 4, wherein said binding agent is chemically tethered to said oligonucleotide at an internal site of said oligonucleotide.*

*51. A method as recited in claim 24, wherein said binding agent is chemically tethered to said oligonucleotide at the 3' end of said oligonucleotide.*

*52. A method as recited in claim 24, wherein said binding agent is chemically tethered to said oligonucleotide at the 5' end of said oligonucleotide.*

*53. A method as recited in claim 24, wherein said binding agent is chemically tethered to said oligonucleotide at an internal site of said oligonucleotide.*

* * * * *